United States Patent [19]

Endress

[11] Patent Number: 4,541,554

[45] Date of Patent: Sep. 17, 1985

[54] SOCK STRETCHER

[76] Inventor: Donald A. Endress, HC 65, Box 1700, Hominy, Okla. 74035

[21] Appl. No.: 685,895

[22] Filed: Dec. 24, 1984

[51] Int. Cl.⁴ .................. D06C 15/00; D06C 5/00
[52] U.S. Cl. ........................................... 223/66; 223/77
[58] Field of Search .................. 223/75, 76, 77, 61, 223/72, 74, 25, 15, 63, 65, 66; 26/80; 34/103, 104

[56] References Cited

U.S. PATENT DOCUMENTS

| | | | |
|---|---|---|---|
| 342,049 | 5/1886 | Spitzer | 223/61 |
| 594,963 | 12/1897 | Orfeur | 223/61 |
| 686,314 | 11/1901 | Mansfield | 34/104 |
| 1,038,792 | 9/1912 | Schlosser | 223/61 |
| 1,104,188 | 7/1914 | Hammock | 223/63 |
| 1,608,352 | 11/1926 | Young | 223/63 |
| 1,990,013 | 2/1935 | Albrecht | 223/61 |
| 2,065,372 | 12/1936 | Johnston | 223/61 |
| 2,156,349 | 5/1939 | Oldfield | 223/77 |
| 2,519,276 | 8/1950 | Needles et al. | 223/61 |
| 3,103,302 | 9/1963 | Minton | 223/72 |
| 3,273,765 | 9/1966 | Pillola | 223/72 |
| 3,471,068 | 10/1969 | Foreman | 223/61 |
| 3,779,433 | 12/1973 | Imai | 223/66 |

*Primary Examiner*—Louis K. Rimrodt
*Assistant Examiner*—Joseph S. Machuga
*Attorney, Agent, or Firm*—William S. Dorman

[57] ABSTRACT

A sock stretcher comprising a plurality of hollow and generally cylindrical sleeves telescopically arranged within each other, the sleeves having progressively smaller outside diameters such that a second and next largest sleeve would have an outer diameter somewhat smaller than the inner diameter of a first and largest sleeve, the second sleeve having a radially outwardly directed lip at its upper end adapted to engage with a radially inwardly directed lip at the lower end of the first sleeve in which the second sleeve is received when the sleeves are moved towards an extended telescopic condition. A transverse support bar extends across the first sleeve adjacent the upper end thereof, and a second transverse supporting bar extends across the upper end of the smallest sleeve. A rotatable threaded shaft extends along the longitudinal central axes of the sleeves and threadedly engages a threaded hole at the center of the first transverse bar, the lower end of the threaded shaft being connected to the second bar for movement of the second bar with respect to the first bar, the threaded shaft being freely rotatable with respect to the second bar, and a handle at the upper end of the shaft for rotation of the shaft, whereby a damp sock can be placed over the sleeves in their retracted telescopic condition. The open end of the damp sock can be clamped to the upper end of the first sleeve, whereby, upon rotation of the shaft, the sleeves will move to their fully extended telescopic condition to stretch the damp sock.

6 Claims, 7 Drawing Figures

SOCK STRETCHER

BACKGROUND OF THE INVENTION

1. Field of the Invention

The present invention relates to a device for stretching socks and, more particularly, to a sock stretcher for stretching socks which go over a leg stump or arm stump which is inserted into an artificial leg or artificial arm.

2. Prior Art

When it becomes necessary to amputate an arm or a leg for any reason, oftentimes it is possible to leave a leg stump or arm stump which can be fitted into an artificial arm or leg sometimes referred to as a prosthesis. The prosthesis will have a cavity which conforms in size and shape to the size and shape of the stump. However, care must be taken to provide the proper lining between the stump and the prosthesis to prevent irritation of the stump. A woolen sock is customarily employed directly over the stump. The woolen sock used by the amputee is not the same as the conventional woolen sock worn over the normal foot; the woolen sock of the type referred to herein is much thicker than a conventional woolen sock and is also of a much finer weave. Additional cotton socks can be placed over the woolen sock for additional padding or lining, if desired.

The amputee who will be wearing the prothesis described above will perspire during the normal course of events and the woolen sock will absorb perspiration from the stump. This means that the sock which covers the stump must be washed every day. This also means that the sock, being made of wool, will shrink unless steps are taken to prevent its shrinkage. The woolen sock of the type referred to herein, being thicker and of a finer weave than a conventional woolen sock is very difficult to stretch. After several washings, the woolen sock begins to become too small to use. Amputees have tried to stretch these socks over ice tea glasses and boards which are shaped to conform with the longitudinal cross-sectional shape of the sock, but, still, after twenty or thirty washings, the socks become unusable. Other attempts have been made to deal with this problem, but no satisfactory solution has been reached prior to the present invention.

A preliminary patentability search was conducted on the present invention and the following listed United States patents were uncovered in the search.

| | | |
|---|---|---|
| 342,049 | 1,990,013 | 3,103,302 |
| 594,963 | 2,065,372 | 3,273,765 |
| 1,038,792 | 2,519,276 | 3,471,068 |

None of the above patents are considered to be sufficiently pertinent as to require any comment.

SUMMARY OF THE INVENTION

The present invention involves a sock stretcher for stretching a sock of the type normally worn over an arm stump or leg stump which is interfitted with an artificial prosthesis. The sock stretcher comprises three sleeves each in the form of a hollow cylinder, nested one within the other and disposed in a generally vertical direction. The sleeves can telescope from an extended telescopic condition to a retracted telescopic condition. The middle sleeve has an outer diameter somewhat smaller than the inner diameter of the outer sleeve. The middle sleeve has a circumferential lip at its upper end which extends radially outwardly towards the inner surface of the outer sleeve. The outer sleeve has a lip at its lower end which projects radially inwardly towards the outer surface of the middle sleeve. A similar lip arrangement is provided at the top of the inner sleeve and the bottom of the middle sleeve. The sleeves can telescope outwardly until the outwardly extending lips described above come into contact with the inwardly projecting lips on the adjacent outerlying sleeves.

Movement of the sleeves to their extended telescopic condition, or to their retracted telescopic condition is effected by an alongated threaded shaft which is mounted along the vertical central axes of the sleeves. The outermost sleeve is provided with a transverse bar extending diametrically across this sleeve below the top thereof. The threaded shaft passes through a threaded hole in the center of this first transverse bar. A second transverse bar is mounted adjacent the top of the innermost sleeve. The lower end of the threaded shaft is connected to the second bar so as to be able to exert a force against the bar in both directions of movement, but the lower end of the threaded shaft is freely rotatable with respect to this second bar. A handle is provided at the upper end of the threaded shaft to permit the turning thereof.

If it is desired to stretch a sock of the type referred to above with the sock stretcher of the present invention, the open end of the sock is inserted over the sleeves in their retracted telescopic condition. The open end of the sock will be adjacent the top of the outermost sleeve. The top of the sock will be secured to the top of the outermost sleeve by a suitable cicumferential clamp. Now the handle is turned to rotate the threaded shaft in a given rotary direction to move the sleeves towards their extended telescopic condition. After the sleeves have been extended to the requisite distance, the sock stretcher is put to one side so that the sock can dry thereon. After the sock has dried, the clamp is released and the sock is removed. Preferably, the sleeves are downwardly and inwardly tapered.

DETAILED DESCRIPTION OF THE PREFERRED EMBODIMENTS

Figures 1, 2, 3:
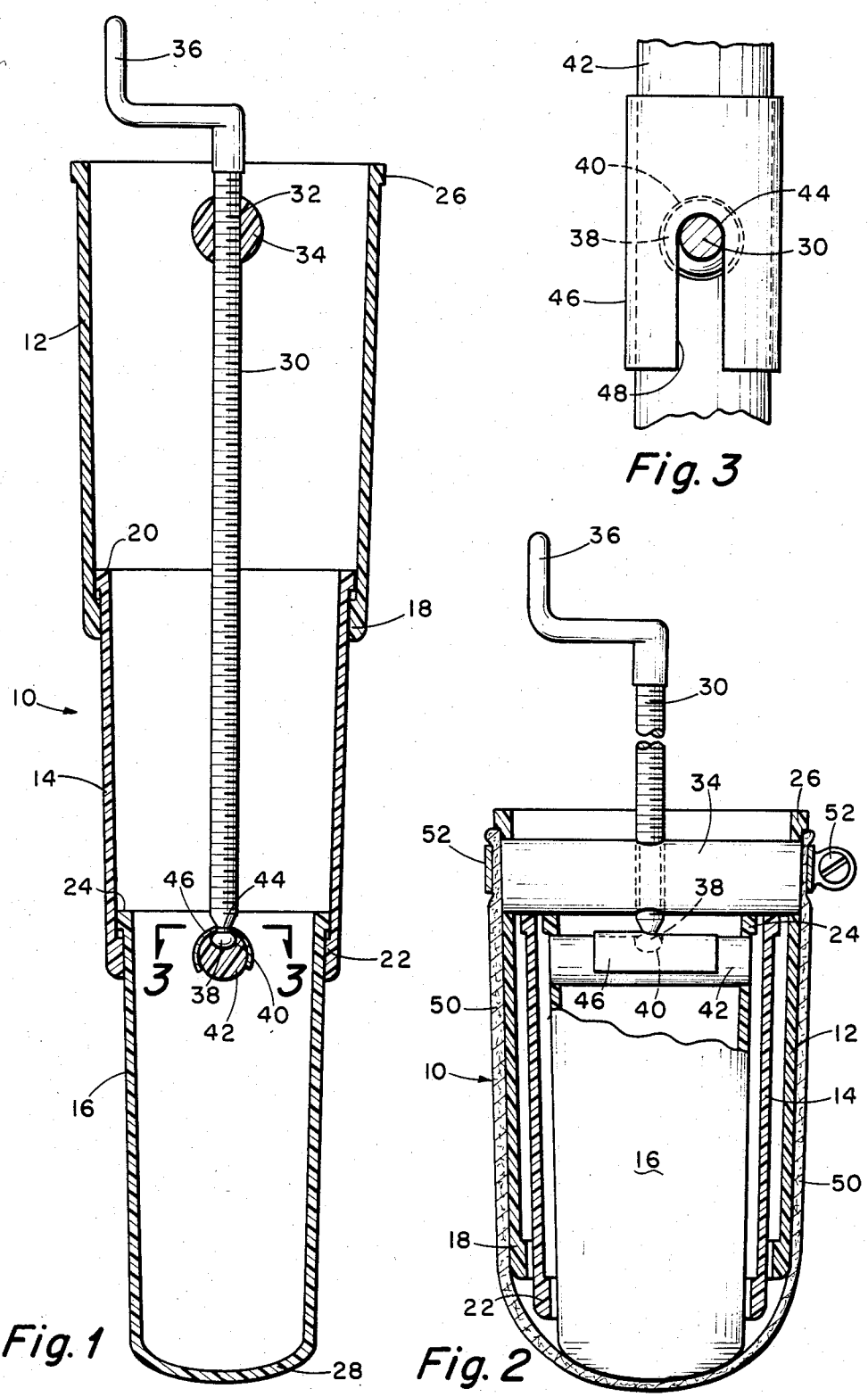
FIG. 1 is a longitudinal cross sectional view through the sock stretcher of the present invention with the sleeve elements shown in their fully extended telescopic condition.
FIG. 2 is a longitudinal cross sectional view of the device shown in FIG. 1 with the sleeve elements in their fully retracted telescopic condition and also showing, in cross section, a woolen sock received over the sock stretcher.
FIG. 3 is a fragmentary cross sectional view taken along section line 3—3 of FIG. 1.

Referring to the drawings in detail, FIGS. 1 and 2 show a sock stretcher 10 comprising three generally cylindrical members or sleeves 12, 14, and 16. Although three such cylindrical members are shown, it should be understood that the sock stretcher of the present invention could be composed of two cylindrical members or more than three cylindrical members, if desired. The cylindrical members or sleeves are preferably made of durable plastic material and are hollow and open ended; they are somewhat tapered and telescopically slidable within each other. Thus, the sleeve 12 has an inner diameter which is larger than the outer diameter of the sleeve 14, and the inner diameter of the sleeve 14 is somewhat larger than the outer diameter of the sleeve 16.

The lower end of the sleeve 12 is provided with a radially inwardly directed flange or lip 18 which is adapted to cooperate with a radially outwardly directed flange or lip 20 at the top of the sleeve 14. Similarly, the lower end of the sleeve 14 is provided with an inner lip or flange 22 which cooperates with an outwardly directed flange or lip 24 at the top of the sleeve 16. The upper end of the sleeve 12 is also provided with an outwardly projecting lip or flange 26 so that this cylinder can, if desired, cooperate with the lower lip of an even larger sleeve (not shown) in which the sleeve 12 could be slidably and telescopically received.

The lower end 28 of the smallest sleeve 16 is shown as being closed over and rounded; however, it should be understood that the lower end of the sleeve 16 could also be provided with an inwardly directed flange or lip (not shown) similar to the lips 18 and 22, in the event that it was desired to use a further sleeve (not shown) smaller than the sleeve 16 and which would be slidably and telescopically received within the sleeve 16. Of course, in such a circumstance the lower end of the sleeve 16 would be open as is the case with the sleeves 12 and 14.

In FIG. 1, the sleeves 12, 14, and 16 are shown essentially in their fully extended telescoping relationship; in FIG. 2 these same elements 12, 14, and 16 are shown in their fully retracted telescoping relationship.

In order to move the elements from their respective positions shown in FIG. 1 to the positions shown in FIG. 2, and vice versa, an elongated threaded shaft or rod 30 is mounted for rotation within the members 12, 14, and 16 along their longitudinal central axes. The upper end of the threaded rod or shaft 30 (as it appears in FIG. 1) is threadedly received within a threaded hole 32 in a cylindrical bar or cross member 34. This cross member 34 is preferably made of nylon or other durable plastic material capable of receiving and maintaining a threaded opening therethrough. The ends of the cross member or bar 34 are connected to the sides of the sleeve 12 below the lip 26 such that the bar 34 extends diametrically or transversely across the sleeve 12. An L-shaped handle 36 is attached to the upper end of the threaded rod 30 to permit the turning thereof.

The lower end of the threaded rod 30 (below the threaded portion thereof) is provided with a ball 38 of reduced diameter (with respect to the diameter of the threaded portion of the rod). The ball 38 is adapted to be received in a spherical recess 40 in a cylindrical cross member 42 which is similar to, but preferably smaller than, the cross member 34. The cross member 42 is connected to the sides of the lower sleeve 16 below the upper lip 24 thereof in essentially the same manner that the cross member 34 is connected to the sleeve 12. Both the cross members 34 and 42 can be glued or fused to the sides of their respective sleeves 12 and 16.

In order to hold the ball 38 in the recess 40, the rod 30 is provided with an annular groove 44 immediately above the ball. An arcuate clip 46 is adapted to be received on the cross member 42 and is horizontally slidably thereon. As best shown in FIG. 1, this clip 46 engages the outer surface of the cross member 42 for more than 180° so that it cannot be easily pulled off. Of course, the clip 46 will be sufficiently flexible that it can be forced onto the cross member 42 to snap into the position shown in FIGS. 1, 2, and 3. As best shown in FIG. 3, the upper end of the clip 46 is provided with a horizontal slot 48 whose width is equal to the inner diameter of the annular groove or recess 44 above the ball 38. If it is desired to release the ball 38 from its engagement with the sperical recess 40 in the cross member 32, one can slide the clip 46 to the left (as it appears in FIG. 2) or upwardly (as it appears in FIG. 3) until the slot 48 is out of engagement with the recess 44 and so that the ball 38 can clear the edge of the clip 46.

Summarizing, the sleeves 12, 14, and 16 can be moved from their respective positions shown in FIG. 1 to their positions shown in FIG. 2, and vice versa, by merely turning the handle 36 and rotating the shaft 30 in a given rotary direction. Now, it if were desired to stretch a woolen sock of the type worn over the stub of an amputated leg or arm, for example, such a (damp) sock 50 (see also FIG. 4) would be placed over the device 10 when the elements occupied their respective positions shown in FIG. 2. The upper open end of the sock would be secured or clamped to the upper end of the sleeve 12 by means of a clamp 52. This clamp 52 is shown as the conventional type of metal strap which is used for connecting the ends of hoses over pipes and which can be tightened simply by a screw driver. Obviously, any other type of suitable clamp could be employed, if desired.

Figure 4:
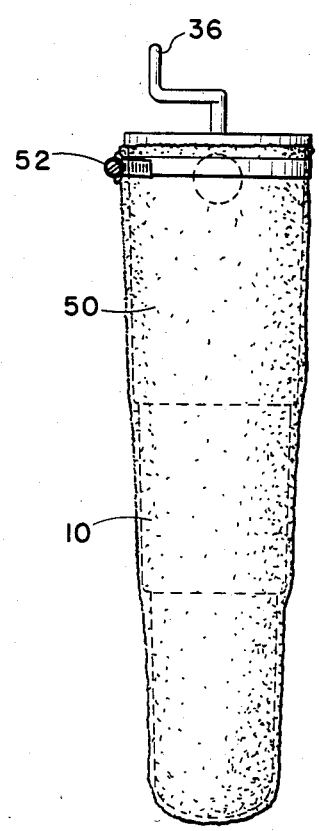
FIG. 4 is a side elevation similar to FIG. 1, but on a smaller scale, showing the sock of FIG. 2 in its fully stretched condition.

After the (damp) sock 50 is slipped over the elements shown in FIG. 2 and the clamp 52 is applied, the handle 36 can be rotated to move the sleeves 12, 14, and 16 into their outwardly telescoped positions as shown in FIGS. 1 and 4. The damp sock shown in FIG. 4 is now in its stretched condition and will be allowed to remain on the sock stretcher 10 in the FIG. 4 position until the sock has dried, at which time it will be essentially the same size as a new sock.

Figure 6:
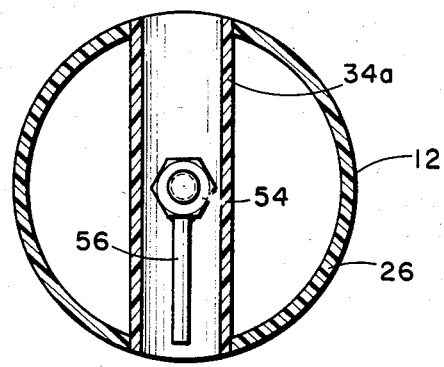
FIG. 6 is a transverse sectional view taken along section line 6—6 of FIG. 5.
Figure 5:
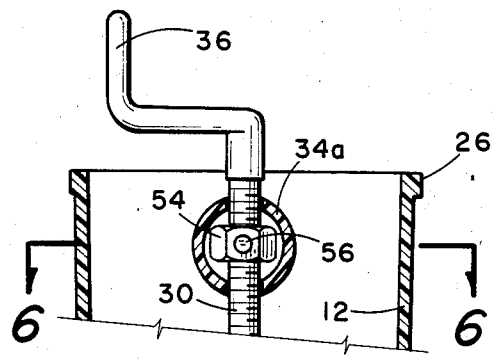
FIG. 5 is a fragmentary cross sectional view of a modified connection between the upper part of the threaded rod and the upper transverse bar.

Although the cross member 34 has been described as being a solid cylindrical member preferably made of nylon, it is possible to use a hollow cylindrical cross member 34a as shown in FIGS. 5 and 6. In such a case, the threaded rod 30 would engage a nut 54 received on the rod 30 in the interior of the hollow cross member 34a. The nut 54 could be restrained from rotating by means of an elongated pin or rod 56 attached to one side of the nut 54 and extending longitudinally within the cross member 34a.

Figure 7:
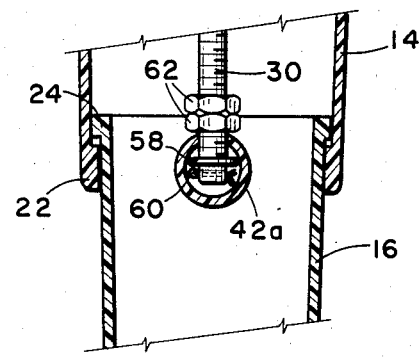
FIG. 7 is a fragmentary longitudinal cross sectional view showing a modified type of condition between the lower end of the threaded rod and the lower transverse cross member.

Although the lower end of the threaded rod 50 was previously described in terms of a ball 38 which was received in a spherical recess 40 in the cross member 42, it is possible to employ a hollow cross member 42a as shown in FIG. 7. In such a case, the lower end of the threaded rod 30 would simply extend through an opening on the upper side of the cross member 42 and through a washer 58 which would be received within the hollow portion of the cross member 42a. A cotter pin 60 would pass through a suitable transverse hole in the shaft 30 below the washer 58 to permit retracting of the lower sleeve 16. For the purposes of extension, a pair of lock nuts 62 are received on the shaft 30 immediately above the cross member 42a. The lower nut of the two lock nuts 62 constitutes a bearing surface which exerts a force on the cross member 42a to move the lower sleeve 16 towards its extended telescoping position.

Whereas the present invention has been described in particular relation to the drawings attached hereto, it should be understood that other and further modifications, apart from those shown or suggested herein, may be made within the spirit and scope of this invention.

What is claimed is:

1. A sock stretcher for stretching a sock of the type normally worn over an arm stump or leg stump which is interfitted with an artificial prosthesis comprising a plurality of sleeves each in the form of a hollow cylinder, nested coaxially one within the other and disposed with their central axes in a generally vertical direction for the purpose of this claim description, each sleeve having an inner diameter slightly larger than the outer diameter of the next adjacent inner sleeve, each sleeve having a lip at its lower end which projects radially inwardly towards the outer surface of the next adjacent inner sleeve, each inner sleeve having a circumferential lip at its upper end which extends radially outwardly towards the inner surface of the next adjacent outer sleeve, whereby the sleeves can telescope outwardly until the outwardly extending lips come into contact with the inwardly projecting lips on the next adjacent outerlying sleeves, an elongated threaded shaft mounted along the vertical central axes of the sleeves, the outermost sleeve being provided with a first transverse bar extending diametrically across this sleeve below the top thereof, the threaded shaft passing through a threaded means mounted in the center of this first transverse bar, a second transverse bar mounted adjacent the top of the innermost sleeve, the lower end of the threaded shaft being connected to the second bar so as to be able to exert a force against this bar in both directions of movement, but the lower end of the threaded shaft being freely rotatable with respect to this second bar, a handle mounted at the upper end of the threaded shaft to permit the turning thereof, whereby a damp sock of the type referred to herein can be inserted over the sleeves in their retracted telescopic condition such that the upper open end of the sock will be adjacent the top of the outermost sleeve, the top of the sock then being secured to the top of the outermost sleeve by a suitable clamp, the handle then being turned to rotate the threaded shaft in a given rotary direction to move the sleeves towards their extended telescopic condition to stretch the sock a desired amount.

2. A sock stretcher as set forth in claim 1 wherein the sleeves are downwardly and inwardly tapered.

3. A sock stretcher as set forth in claim 1 wherein the threaded means at the center of the first transverse bar is constituted by a threaded hole through the center of the first transverse bar.

4. A sock stretcher as set forth in claim 1 wherein the threaded means at the center of the first transverse bar is constituted by a threaded nut mounted in the center of the first transverse bar and restrained from rotation with respect to the first bar.

5. A sock stretcher as set forth in claim 1 wherein the lower transverse bar is cylindrical, the lower end of the threaded shaft being provided with a ball whose diameter is slightly less than the diameter of the shaft, the ball being received in a spherically shaped recess in the upper portion of the second bar, the shaft being provided with an annular groove immediately above the ball, a flexible and transversely slidable arcuate clip engaging the outer surface of the second bar for more than 180°, the clip being provided with a horizontal slot whose width is equal to the inner diameter of the annular groove above the ball, whereby the clip can be moved slidably along the second bar until the horizontal slot is received in the annular groove to hold the ball in the spherically shaped recess.

6. A sock stretcher as set forth in claim 1 wherein the lower transverse bar is hollow and cylindrical, the lower end of the threaded shaft passing through a hole in the second bar and into the hollow interior thereof, a washer mounted on the threaded shaft in the interior of the second bar, a cotter pin on the threaded shaft below the washer to hold the washer on the shaft, and a pair of lock nuts mounted on the threaded shaft above the second bar and engagable with the second bar to exert a downward force against the second bar upon rotation of the shaft in a given rotary direction.

* * * * *